United States Patent [19]

Prencipe et al.

[11] Patent Number: 5,578,293

[45] Date of Patent: *Nov. 26, 1996

[54] ORAL COMPOSITIONS CONTAINING STABILIZED STANNOUS COMPOUNDS HAVING ANTIPLAQUE AND ANTITARTAR EFFICACY

[75] Inventors: Michael Prencipe, Princeton; Michael Burke, Somerset; Suryakant Patel, Bridgewater; Julie A. Miller, Somerset, all of N.J.

[73] Assignee: Colgate Palmolive Company, New York, N.Y.

[ * ] Notice: The term of this patent shall not extend beyond the expiration date of Pat. No. 5,487,906.

[21] Appl. No.: 350,309

[22] Filed: Dec. 6, 1994

[51] Int. Cl.$^6$ .............. A61K 7/16; A61K 7/18; A61K 7/24

[52] U.S. Cl. .............. 424/49; 424/52; 424/55; 424/57

[58] Field of Search ............ 424/49–58

[56] References Cited

U.S. PATENT DOCUMENTS

| | | | |
|---|---|---|---|
| 3,105,013 | 9/1963 | Saul | 167/93 |
| 3,282,792 | 11/1966 | Fiscella | 167/93 |
| 4,011,309 | 3/1977 | Lutz | 424/49 |
| 4,335,102 | 6/1982 | Nakashima et al. | 424/52 |
| 4,340,583 | 7/1982 | Wason | 424/52 |
| 4,363,794 | 12/1982 | Ochal et al. | 424/52 |
| 4,418,057 | 11/1983 | Groat et al. | 424/151 |
| 4,533,544 | 8/1985 | Groat et al. | 424/52 |
| 5,017,363 | 5/1991 | Suhonen | 424/52 |
| 5,094,842 | 3/1992 | Riley | 424/52 |
| 5,096,702 | 3/1992 | Rolla et al. | 424/52 |
| 5,145,666 | 9/1992 | Lukacovic et al. | 424/52 |
| 5,188,820 | 2/1993 | Cummins et al. | 424/49 |
| 5,240,697 | 8/1993 | Norfleet et al. | 424/52 |
| 5,250,402 | 10/1993 | Prencipe et al. | 424/53 |
| 5,258,173 | 11/1993 | Waterfield | 424/49 |
| 5,281,410 | 1/1994 | Lukacovic et al. | 424/49 |
| 5,281,411 | 1/1994 | Majeti et al. | 424/52 |
| 5,292,502 | 3/1994 | Burke et al. | 424/54 |
| 5,296,215 | 3/1994 | Burke et al. | 424/49 |
| 5,320,830 | 6/1994 | Lukacovic et al. | 424/52 |
| 5,320,831 | 6/1994 | Majeti et al. | 424/52 |
| 5,352,439 | 10/1994 | Norfleet et al. | 424/52 |
| 5,374,417 | 12/1994 | Norfleet et al. | 424/49 |

Primary Examiner—Shep K. Rose
Attorney, Agent, or Firm—Paul Shapiro

[57] ABSTRACT

An aqueous oral care composition containing a stannous ion releasing compound and a combination of a pyrophosphate salt, and an organic acid compound, the combination being present in the composition in an amount sufficient to effectively stabilize the stannous ion concentration.

20 Claims, No Drawings

ORAL COMPOSITIONS CONTAINING STABILIZED STANNOUS COMPOUNDS HAVING ANTIPLAQUE AND ANTITARTAR EFFICACY

BACKGROUND OF THE INVENTION

1. Field of the Invention

This invention relates to aqueous oral care compositions containing stannous compounds having increased stannous ion stability. In particular, this invention is directed to compositions containing stannous compounds stabilized with a combination of a water-soluble pyrophosphate salt and an organic acid compound. The compositions of the invention are particularly useful in the form of aqueous toothpaste, aqueous mouthwash and aqueous gel compositions exhibiting improved antitartar and antiplaque activity.

2. The Prior Art

There have been many proposals in the prior art to incorporate stannous compounds into oral health care products for the purpose of achieving particular clinical benefits such as caries prevention, plaque control and the reduction of gingivitis. Upon association with water or saliva, these stannous compounds release stannous ions which are active against oral bacteria and provide the desired benefits.

U.S. Pat. No. 3,956,479 discloses the use of quaternary anticalculus compounds in dental creams, containing polishing agents such as water-insoluble phosphates, binders, detergents, gelling agents, flavoring agents, and fluoride-containing compounds including stannous fluoride.

U.S. Pat. Nos. 3,711,604, 3,919,409, 3,935,306 and 3,980,767 disclose dentifrice formulations containing water soluble fluoride compounds, including stannous fluoride. The toothpaste formulations also include gelling agents such as carboxyvinyl polymers and insoluble abrasives such as silica and silicates.

U.S. Pat. No. 4,254,101 discloses compositions containing a humectant, silica abrasive, a carboxyvinyl polymer, water and fluoride compounds as optional ingredients. A variety of fluoride compounds including stannous fluoride are described as suitable optional ingredients. Phosphorus-containing anticalculus agents are also listed as optional ingredients.

U.S. Pat. No. 4,515,772 discloses oral compositions containing certain pyrophosphate salts as anticalculus formulations. A number of chelating agents are proposed as anticalculus agents, including ethylenediaminetetraacetic acid, nitrilotriacetic acid, polyphosphonates and carbonyl diphosphonates. An extensive list of fluoride ion sources is provided, including stannous fluoride.

U.S. Pat. No. 4,627,977 discloses dentifrice compositions containing a calculus-inhibiting amount of a linear molecularly dehydrated polyphosphate salt, and to inhibit hydrolysis of the polyphosphate salt in the saliva, a combination of a fluoride ion-providing source and a synthetic linear polymeric polycarboxylate. An extensive list of fluoride ion sources are provided, including stannous fluoride.

Formulations which contain stannous compounds such as stannous fluoride exhibit excellent clinical benefits, particularly in the reduction of gingivitis but have not been widely used in aqueous oral care formulations because of stability problems as the stannous ion is unstable and tends to react with other ingredients of the oral care composition to form insoluble inactive tin compounds, thereby reducing the effective amount of available stannous ion in the composition. Presently available commerical formulations contain $SnF_2$ in anhydrous gels because of the instability of stannous ion in aqueous environments.

Numerous stannous compound oral care compositions with "stabilizing agents" have been proposed by the art.

U.S. Pat. No. 3,282,792 discloses the use of hydroxyl-substituted aliphatic di- and tri-carboxylic acids e.g. citric acid and malic acid as stabilizers for stannous fluoride in aqueous dentifrice compositions.

U.S. Pat. No. 3,445,567 discloses that aqueous stannous fluoride compositions can be stabilized with sorbitol or a mixture of sorbitol and glycerin.

U.S. Pat. No. 4,418,057 discloses a stannous fluoride oral care composition formulated as a non-aqueous gel mixture including anhydrous glycerin and an hydroxyethyl cellulose gelling agent. Total exclusion of moisture from the gel is required to protect the stannous ion.

U.S. Pat. No. 4,902,497 discloses dentifrices containing $SnCl_2$ and gluconic acid.

U.S. Pat. No. 5,004,597 discloses an aqueous composition containing stannous fluoride wherein stannous chloride and stannous gluconate constitute a stannous reservoir to replace unstable stannous ion.

U.S. Pat. No. 5,017,363 discloses stannous fluoride toothpaste compositions containing an alkyl vinyl ether and maleic anhydride or acid copolymer as a stabilizing agent for stannous fluoride the composition being substantially free of soluble pyrophosphate salts, silica containing compounds and aldehyde group containing compounds.

U.S. Pat. Nos. 5,145,666 and 5,281,411 disclose a two component oral composition wherein one component contains stannous fluoride and stannous gluconate and the second component contains a pyrophosphate, the components being maintained separately before use.

U.S. Pat. No. 5,213,790 discloses a two component dentifrice wherein one component contains stannous fluoride and stannous gluconate and the other component contains a citrate ion source.

U.S. Pat. No. 5,281,410 discloses a two component oral composition wherein one component contains stannous fluoride and a stannous salt of an alpha hydroxy acid and a second component containing a pyrophosphate ion source.

U.S. Pat. No. 5,281,411 discloses dentifrices containing stannous gluconate and sodium monofluorophosphate and less than 0.05% stannous fluoride.

U.S. Pat. No. 5,258, 173 discloses the use of an antioxidant such as butylated hydroxy anisole in stannous fluoride dentifrices to reduce or prevent the conversion of stannous ions to stannic ions.

SUMMARY OF THE INVENTION

The present invention provides an aqueous composition for oral care, containing a stannous compound such as stannous fluoride, and a combination of a water soluble pyrophosphate salt and an organic acid compound which are present in the composition in an amount sufficient to effectively stabilize the stannous ion concentration. The composition containing the stabilized stannous compound is found to exhibit improved antitartar(anticalculus), antiplaque and antigingivitis activity.

As will hereinafter be demonstrated, it is an essential and critical feature of the present invention that the combination of organic acid compound and water soluble pyrophosphate salt must all be present together in the oral care composition of the present invention in order that the stannous compound incorporated therein be effectively stabilized.

DESCRIPTION OF THE PREFERRED EMBODIMENTS

An oral care composition containing a stannous compound which is "effectively stabilized" means that the stannous ion concentration in the composition after 12 weeks storage at 105° F. remains at an acceptable therapeutic level, i.e., the stannous ion concentration remaining in the oral care composition after such storage conditions is equivalent to about 70 percent or more of the original concentration of stannous ion at the time of formulation of the composition. Product stability after 12 weeks at 105° C. is comparable to product stability after 2–3 years at room temperature.

The vehicle used for the preparation of the oral composition of the present invention will normally include water, humectant, surfactant and polishing agent. The water and humectant comprise the liquid portion of the composition. The humectant component will preferably comprise a mixture of humectants, such as glycerin, sorbitol and a polyethylene glycol having a molecular weight in the range of 200–1000, but other mixtures of humectants and single humectants may also be employed.

The humectant content in the oral compositions of the present invention is generally in the range about of 10% to about 80% by weight and preferably about 40 to about 50% by weight. The water content is in the range of about 3 to about 40% by weight and preferably 5 to 30% by weight.

Suitable stannous salts which may be used in the compositions of the present invention include water soluble stannous salts such as stannous fluoride and stannous chloride.

Stannous fluoride is present in the oral compositions of the present invention at a concentration of about 0.05 to about 2% by weight and preferably about 0.2 to about 1% by weight, it should be recognized that separate soluble stannous and fluoride salts may be used to form stannous fluoride in situ as well as adding the stannous fluoride salt directly to the composition.

When stannous chloride is present in the oral compositions of the present invention, the salt is present at a concentration of about 0.25 to about 5.0% by weight and preferably 0.5 to about 2% by weight.

The water soluble pyrophosphate salt used in the present invention can be any of the water soluble alkali metal pyrophosphates including dialkali metal pyrophosphates and tetraalkali metal pyrophosphates, such as disodium pyrophosphate, dipotassium pyrophosphate, tetrapotassium pyrophosphate and tetrasodium pyrophosphate. The amount of the pyrophosphate salt incorporated in the compositions of the present invention range from about 0.5 to about 5% by weight and preferably about 0.5 to about 2.0% by weight.

The term "organic acid compound" includes within its meaning the free acid or its water soluble salt The concentration of organic acid compound, that is, the organic acid or its water soluble salt, used in the practice of the present invention, is in the range of from about 0.01 to about 10% by weight and preferably from about 0.5 to about 5% by weight.

Suitable organic acid compounds useful in the practice of the present invention include polycarboxylic food grade organic acids such as citric acid, lactic acid, tartaric acid, gluconic acid, succinic acid, malic acid, fumaric acid and their water soluble salts such as the alkali metal salts including sodium or potassium citrate and sodium or potassium lactate.

Inorganic thickeners may be incorporated in the compositions of the present invention, and especially useful in the practice of the present invention are silicas such as Sylox 15 available from W. R. Grace Corporation, that is, finely divided silica having a density of about 0.10–0.20 g/cc, an average particle size less than about 10 microns and preferably about 2 microns or less. The inorganic thickener may be incorporated in the compositions of the present invention at a concentration of about 0.5 to about 10% by weight and preferably about 1 to about 5% by weight.

Organic thickeners of natural and synthetic gums as colloids may also be incorporated in the compositions of the present invention. Among these may be mentioned carrageenan (Irish moss), xanthan gum and carboxymethyl cellulose, which are preferred, and also starch, polyvinylpyrrolidone, hydroxyethylpropylcellulose, hydroxybutyl methyl cellulose, hydroxypropyl methyl cellulose, and combinations thereof. The organic thickener may be incorporated in the compositions of the present invention at a concentration of about 0.1 to about 3% by weight and preferably about 0.2 to about 2% by weight.

Surface active agents may be incorporated in the dentifrices of the present invention to provide foaming properties and also aid in producing a uniform composition in which the ingredients of the composition are evenly distributed. The surface-active material is preferably anionic, nonionic or ampholytic in nature, and most preferably is anionic. Suitable examples of anionic surfactants are higher alkyl sulfates such as potassium or sodium lauryl sulfate, sodium lauryl sulfoacetate, higher fatty acid monoglyceride monosulfates, such as the potassium salt of the monosulfated monoglyceride of hydrogenated coconut oil fatty acids, alkyl aryl sulfonates such as potassium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the potassium salts of N-lauroyl, N-myristoyl, or N-palmitoyl sarcosine.

Examples of water soluble nonionic surfactants are condensation products of ethylene oxide with various hydrogen-containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic materials).

The surface active agent is generally present in the compositions of the present invention at a concentration of about 0.5 to about 5.0% by weight and preferably about 0.75 to about 2.0% by weight.

Abrasives may be incorporated in the dentifrices of the present invention and preferred abrasives are siliceous materials, such as silica, and preferably a precipitated amorphous hydrated silica, such as Zeodent 115, marketed by Huber Corporation, but other abrasives may also be employed, including water-insoluble sodium metaphosphate, potassium metaphosphate, anhydrous alumina trihydrate, aluminum silicate, zirconium silicate, calcined alumina and bentonite. The abrasive is generally present in the compositions of the present invention at a concentration of about 10 to about 40% by weight and preferably about 15 to about 30% by weight.

Other components which may be incorporated in the dentifrice of the present invention, include dyes, pigments, sweetener, flavor and preservative. In white dental cream formulations the pigment is preferably titanium dioxide, and the proportion thereof will normally be in the range of 0.2 to 3% by weight, preferably 0.5 to 1.0% by weight. The sweetener content will normally be that of an artificial or synthetic sweetener and the normal proportion thereof present will be in the range of 0.1 to 1.0% by weight, preferably 0.3 to 0.7% by weight. The flavor content, which is preferably of a mixed peppermint/menthol flavor, will usually be in the range of 0.5 to 2% by weight, preferably 0.5 to 1.5% by weight. F.D. & C grade dyes may be used in appropriate amounts to provide desired colors. The contents of other components or adjuvants of the toothpaste formula will normally not exceed 10% by weight, often will be less than 5% by weight, and can be as low as 0%. Examples of such adjuvants include antibacterial agents including halogenated diphenyl ethers such as Triclosan and chlorhexidene and potassium salts such as potassium nitrate and potassium citrate for the treatment of dentin hypersensitivity as well as peroxide whitening agents such as hydrogen peroxide and urea peroxide.

A dentifrice may be prepared in accordance with the present invention by first adding stannous compounds mixed to a portion of the water or humectant to be used in the preparation of the dentifrice which may be heated to facilitate dissolution to prepare a premix. The premix is then dispersed in the remaining water, humectant, along with thickener, sweetener, organic acid compound, pyrophosphate salt, dye or pigment in a conventional mixer until a slurry forms which is smooth in appearance. The mixture is heated to 100°–120° F. for 10–30 minutes to produce a homogeneous gel phase. The gel phase is transferred to a vacuum mixer and abrasive material is added and mixed for 10–30 minutes at high speed under vacuum in the range of 5 to 100 millimeter of mercury pressure, (mm Hg) preferably 5 to 50 mm Hg to provide a homogenous paste. The surfactant and flavor may then be added to the paste which is followed by mixing another 5 to 10 minutes under vacuum of 5 to 50 mm Hg. The resultant product is a stable dentifrice having a toothpaste or gel texture having a pH in the range of 3 to 7, preferably 5.0 to 6.5, and of satisfactory flavor.

As to other embodiments of the invention, oral care compositions of the present invention may be made in substantially the same manner, with normal adjustments of the formula components and proportions known to those of skill in the oral cam formulation art. To make mouthwashes or other liquid preparations, the main active ingredients may be dissolved or dispersed in an appropriate liquid medium, usually an aqueous alcoholic medium, and insoluble materials will normally be omitted. Other types of oral compositions and preparations may be prepared by appropriate conventional procedures, with appropriate additions of the usual active ingredients and of the appropriate usual supplements and adjuvants during the manufacturing process.

The following examples are further illustrative of the present invention, but it is understood that the invention is not limited thereto. All amounts and proportions referred to herein and the appended claims are by weight.

Example I

A toothpaste containing the ingredients listed in Table I was prepared following the procedure previously described.

TABLE I

| Ingredient | Weight Percent |
| --- | --- |
| Glycerin | 25.946 |
| Carboxymethyl Cellulose | 0.600 |
| Sodium Saccharin | 0.200 |
| Sorbitol (70%) | 20.000 |
| Sodium Citrate Dihydrate | 3.000 |
| Citric Acid | 0.600 |
| Tetrasodium Pyrophosphate | 2.000 |
| Deionized Water | 20.000 |
| $TiO_2$ | 0.500 |
| $SnF_2$ | 0.454 |
| $SnCl_2.2H_2O$ | 1.500 |
| Zeodent 115 | 20.000 |
| Sylox 15 | 3.000 |
| Flavor | 1.000 |
| Sodium Lauryl Sulfate | 1.200 |
| pH | 5.3 |

To determine the stability of the toothpaste of Example I, the toothpaste as prepared was analyzed to determine the amount of stannous ion present. The toothpaste was then stored in plastic laminated tubes and heated in air for 12 weeks at 105° F. Analysis of the stored toothpaste after the twelve week period indicated that the toothpaste contained 0.926% water extractable stannous ion, or that 83% of the original concentration of stannous ion remained in the toothpaste, this result demonstrating that the stannous ion was effectively stabilized.

Example II

The procedure of Example I was repeated to prepare a toothpaste containing a lower concentration of sodium pyrophosphate which composition was designated "Composition A". The ingredients of Composition A are listed in Table II.

The efficacy of Composition A in controlling oral bacteria known to have a role in the development of plaque and gingivitis was assessed by quantifying the level of microflora in human saliva before and after a single brushing with the toothpaste. In this assessment, unstimulated human saliva was collected just prior to and 4 hours after brushing with Composition A. After diluting with sterile buffer, the saliva samples were planted in plates containing trypticase soy agar. The inoculated plates were incubated anerobically for 48 hours at 37° C., and colony forming units were measured using a colony counter. The number of colonies present on the plates before and after brushing was translated into % Reduction of Colony Forming Units (CFU's) vs. baseline. In this test procedure the higher the % reduction of CFU's, the more effective the toothpaste is in controlling oral plaque bacteria. The reduction of CFU's is recorded in Table IV.

For purposes of comparison, the procedure of Example II was repeated except that in separate compositions either the organic acid compound or sodium pyrophosphate was not included in the toothpaste composition. The ingredients of these comparative toothpaste compositions designated "Composition B" which did not contain an organic acid compound and "Composition C" which did not contain a pyrophosphate salt used in Composition A are also listed in Table II. The antiplaque efficacy of Compositions B and C was also assessed in the salivary microflora test used to evaluate Composition A. These results are also recorded in Table III.

TABLE II

| Ingredients | Toothpaste Composition | | |
|---|---|---|---|
| | A | B | C |
| Glycerin | 49.046 | 49.346 | 49.346 |
| Carboxymethyl Cellulose | 0.600 | 0.800 | 0.800 |
| Sodium Sacchaarin | 0.200 | 0.200 | 0.200 |
| Sorbitol | 8.000 | 10.00 | 10.00 |
| Sodium Citrate Dihydrate | 3.000 | — | 5.00 |
| Sodium Pyrophosphate | 0.500 | 4.000 | — |
| Deionized Water | 10.000 | 10.000 | 10.000 |
| $TiO_2$ | 0.500 | 0.500 | 0.500 |
| $SnF_2$ | 0.454 | 0.454 | 0.454 |
| $SnCl_2.2H_2O$ | 1.500 | 1.500 | 1.500 |
| Zeodent 115 | 24.000 | 18.000 | 18.000 |
| Sylox 15 | — | 3.000 | 2.000 |
| Flavor | 1.000 | 1.000 | 1.0 |
| SLS | 1.200 | 1.200 | 1.200 |

TABLE III

| Composition | % Reduction of CFU's vs. Baseline Four Hours After Brushing |
|---|---|
| A | 39.4 |
| B | 0 |
| C | 32.3 |

The results of the salivary microflora study indicate that the % reduction in CFU's four hours after brushing was higher for Composition A than for the comparative Compositions B and C.

Example III

To determine whether the toothpaste of Example I would be effective in tartar control, in vitro testing to determine its potential effectiveness was performed wherein the Example I toothpaste (7.78 grams) diluted with 100 ml water was first centrifuged to obtain a supernatant. One milliliter of the supernatant was diluted 20×with water and hydroxyapatite (HAP) seeds ($68m^2/g$) which were then suspended in the diluted supernatant overnight at 37° C. The treated seeds were then separated from the supernatant and added to a crystal growth solution containing 1.06 mM $CaCl_2$, 0.63 mM $KH_2PO_4$ and 150 mM NaCl. The pH of the growth solution was observed over a 60 minute period, a lowering of the pH being an indication of potential HAP crystal (i.e. tartar) growth, it being known in the art (U.S. Pat. No. 5,139,769) that agents which effectively interfere with the crystalline growth of HAP will be effective as tartar control agents. The pH drop as a function of time was used to measure the rate of crystal growth; the higher the pH drop, the more HAP crystals form.

The results of the HAP crystal growth test are recorded in Table IV below. For purposes of contrast, the test was repeated except that a commercially available toothpaste containing a tartar control agent of known clinical efficacy and a commercial toothpaste containing no tartar control agent were also evaluated. The results are summarized in Table IV below.

TABLE IV

| | pH | | |
|---|---|---|---|
| Time (minutes) | 0 | 30 | 60 |
| Toothpaste | | | |
| Example I | 7.4 | 7.164 | 7.145 |
| Commercial Tartar Control Toothpaste | 7.4 | 7.035 | 6.958 |
| Commercial Toothpaste without tartar control agent | 7.4 | 6.494 | 6.358 |

The results recorded in Table IV indicate that the Example I toothpaste provides potential tartar control efficacy at least equal to a commercial toothpaste known to clinically exhibit tartar control efficacy and is more effective than a commercial toothpaste which does not contain a tartar control agent.

What is claimed is:

1. An aqueous oral care composition consisting essentially of a vehicle having incorporated therein about 0.05 to about 2% by weight of a water soluble stannous ion releasing compound, about 10 to abut 40% by weight of an untreated precipitated silica abrasive and a combination of about 0.05 to abut 2.0% by weight of a water soluble alkali metal pyrophosphate salt and an amount of about 0.01 to about 10% by weight of a polycarboxylic food grade organic acid such amount being sufficient to effectively stabilize the stannous ion, the stabilized stannous ion being present in the composition in an amount effective for therapeutic antiplaque efficacy and the pyrophosphate salt being present in the composition in an amount effective for antitartar efficacy.

2. The composition of claim 1, wherein the stannous ion releasing compound is stannous fluoride.

3. The composition of claim 1 wherein the stannous ion releasing compound is stannous chloride.

4. The composition of claim 3, wherein the stannous chloride is present in the composition at a concentration of about 0.25 to about 5% by weight.

5. The composition of claim 1 wherein the pyrophosphate salt is a water soluble alkali metal pyrophosphate.

6. The composition of claim 1 wherein the pyrophosphate salt is tetrasodium pyrophosphate.

7. The composition of claim 5 wherein the pyrophosphate salt is present in the composition at a concentration of from about 0.5 to about 2.0% by weight.

8. The composition of claim 1 wherein the polycarboxylic acid is citric acid.

9. The composition of claim 1 wherein the organic acid compound is an alkali metal salt of the organic acid.

10. The composition of claim 9 wherein the salt is sodium citrate.

11. A method for the preparation of an aqueous oral composition containing a stable, water soluble stannous ion releasing compound which comprises dispersing about 0.05 to about 2% by weight of the stannous compound in an aqueous vehicle containing a combination about 10 to about 40% by weight of an untreated precipitated silica abrasive about 0.01 to about 10% by weight of an alkali pyrophosphate and about 0.05 to about 2% by weight of an organic acid compound, the amount of said combination being sufficient to effectively stabilize the stannous ion during storage, the stabilized stannous ion being present in the composition in an amount effective for therapeutic antiplaque efficacy and the pyrophosphate salt being present in the composition in an amount effective for antitartar efficacy.

12. The method of claim 11 wherein the stannous ion releasing compound is stannous fluoride.

13. The method of claim 11 wherein the stannous compound is stannous chloride.

14. The method of claim 13 wherein the stannous chloride is present in the composition at a concentration of about 0.25 to about 5% by weight.

15. The method of claim 11 wherein the pyrophosphate salt is a water soluble alkali metal pyrophosphate.

16. The method of claim 11 wherein the pyrophosphate salt is tetrasodium pyrophosphate.

17. The method of claim 15 wherein the pyrophosphate salt is present in the composition at a concentration of from about 0.5 to about 2.0% by weight.

18. The method of claim 1 wherein the polycarboxylic acid is citric acid.

19. The method of claim 11 wherein the organic acid compound is an organic acid salt.

20. The method of claim 19 wherein the salt is sodium citrate.

* * * * *